United States Patent
Sabin et al.

[11] Patent Number: 6,116,231
[45] Date of Patent: *Sep. 12, 2000

[54] LIQUID HEAT PACK

[75] Inventors: Martin W. Sabin, Nokomis; Cullen M. Sabin, Bradenton; Barney J. Guarino, Sarasota, all of Fla.

[73] Assignee: Tempra Technology, Inc., Bradenton, Fla.

[*] Notice: This patent issued on a continued prosecution application filed under 37 CFR 1.53(d), and is subject to the twenty year patent term provisions of 35 U.S.C. 154(a)(2).

[21] Appl. No.: 09/021,927
[22] Filed: Feb. 11, 1998
[51] Int. Cl.$^7$ ........................................ F24J 1/00
[52] U.S. Cl. ........................ 126/263.01; 126/204
[58] Field of Search .............. 126/263.01, 204; 44/266, 250, 251; 604/291; 607/114; 426/114

[56] References Cited

U.S. PATENT DOCUMENTS

| | | | |
|---|---|---|---|
| 2,675,798 | 4/1954 | Rosmarin | 126/204 |
| 3,291,579 | 12/1966 | Mulaskey | 44/266 |
| 3,804,077 | 4/1974 | Williams | 126/263 |
| 4,397,315 | 8/1983 | Patel | 128/403 |
| 4,834,802 | 5/1989 | Prier | 604/291 |
| 4,967,573 | 11/1990 | Wilhelm | 62/530 |
| 5,611,329 | 3/1997 | Lamensdorf | 126/263.07 |
| 5,984,953 | 11/1999 | Sabin et al. | 607/114 |

FOREIGN PATENT DOCUMENTS

| | | | |
|---|---|---|---|
| S56-165856 | 12/1981 | Japan | 126/204 |
| 2233081 | 1/1991 | United Kingdom | 126/204 |

OTHER PUBLICATIONS

Livage, J., et al., Sol–Gel Chemistry of Transition Metal Oxides, *Prog. Solid St. Chem.*, 18:259 (1988).

*Primary Examiner*—Ira S. Lazarus
*Assistant Examiner*—Sara Clarke
*Attorney, Agent, or Firm*—Fish & Richardson PC

[57] ABSTRACT

The invention relates to a self-heating, disposable liquid heating pack utilizing an exothermic chemical reaction. Moderation of the reaction is provided by the use of a gelling agent, which also gives structural rigidity to the heating pack.

29 Claims, 3 Drawing Sheets

LIQUID HEAT PACK

BACKGROUND OF THE INVENTION

The invention relates to self-heating devices for providing heating by exothermic chemical reactions. Compact, self-heating devices that produce heat through exothermic chemical reactions are known to the art. U.S. Pat. No. 4,397,315 discloses a device having an outer envelope and an inner envelope, with the outer envelope containing sodium thiosulfate, and the inner envelope containing ethylene glycol. The walls of the inner envelope are rupturable, allowing the contents of each envelope to mix. U.S. Pat. No. 5,035,230 discloses a heat pack having two compartments separated by a frangible seal. Potassium permanganate oxidizing agent coated with sodium silicate is provided in one zone of the heat pack, and aqueous ethylene glycol fuel is provided in the other zone. In operation of the device, the seal is compromised to allow the reactants to come in contact with each other.

Devices for producing heat or cold by heat of dilution rather than by chemical reaction are also known. U.S. Pat. No. 3,804,077 describes a heat pack which contains a water soluble chemical (e.g., calcium chloride) and a starch material acting as a gelling agent in one zone, and water in another zone.

An aspect of the invention is a disposable container divided into liquid-containing and liquid-impermeable zones.

A further aspect of the invention is a liquid comprising an oxidizing agent, and another liquid comprising a fuel, each liquid in separate zones.

Another aspect of the invention is a non-fuel gelling agent in at least one of the zones.

Yet another aspect of the invention is a separator disposed between zones containing oxidizing agent, and zones containing fuel.

SUMMARY OF THE INVENTION

This invention includes devices and methods for heating. Devices according to this invention include a disposable heat pack which provides heat through a moderated exothermic chemical reaction between particular reactants. The heat pack includes a disposable container divided into two types of zones. The first type of zone contains liquid comprising an oxidizing agent, and, where necessary or desirable, a solvent. The second type of zone contains liquid comprising a fuel, and, where necessary or desirable, a solvent. In one or both types of zones is a non-fuel gelling agent which is ungelled but activatable to form a non-fuel gel. Between the two types of zones is a separator. The separator can be operated or compromised to establish communication between the two types of zones.

Upon operation or compromise of the separator, communication is established between the zones, thereby bringing the two liquids, and hence the oxidizing agent and the fuel, into contact with each other. This initiates an exothermic chemical reaction. The gelling agent is activated to form a gel within the heat pack quickly but not instantaneously.

In general, the invention features a disposable heating device, which is made up of a disposable container having one or more liquid impermeable zones of two types. One of the types of zones contains a liquid oxidizing agent and the other type of zone contains a fuel. A non-fuel gelling agent is present in at least one of the zones. A separator is present between the zone of different types. The separator provides communication between the zones, so that the liquids are mixed. This initiates an exothermic chemical reaction and gelation in the container. A gel is rapidly produced that moderates the rate of the exothermic chemical reaction. The amount of said gelling agent is chosen to produce the gel rapidly enough to prevent the exothermic chemical reaction from causing the container's temperature to overshoot a predetermined maximum temperature.

In a further aspect, the gelation is initiated by the exothermic chemical reaction. In another aspect, the liquids are aqueous liquids, resulting in the chemical reaction occurring in an aqueous environment. In another aspect, the gelation is initiated by a pH change in the aqueous environment.

In another aspect, the container is made of material resistant to the exothermic chemical reaction. The container can also be made of a thin-walled envelope that conforms to the shape of its surroundings, and can also be made of a polymeric material.

In another aspect, the oxidizing agent is an alkali metal salt of permanganate, and can be mixed with a solvent, such as water.

In another aspect, the fuel is a polyhydroxy compound, for example, glycerine, which can also be mixed with a solvent, e.g., water.

In yet another aspect, the heating device of the invention includes a non-fuel gelling agent which includes an inorganic compound, and can be an alkali metal salt of a silicate; an oxidizing agent which includes an alkali metal salt of permanganate; and a fuel which includes a polyhydroxy compound.

In another aspect of the invention, several zones of each of the two types are present.

In a further aspect of the invention, the separator is a single-use, frangible membrane.

In yet another aspect of the invention, the exothermic chemical reaction is a reduction-oxidation reaction.

The invention also generally features a method of heating objects with a heating device as described above. The separator need only be compromised to allow the liquids in the two types of zones to mix thereby initiating an exothermic chemical reaction and a gelation, and warming the object to be heated. Such objects can be foods or drinks, a part of the body of a human or animal surgical patient, or an article of clothing or footwear.

The heat pack of the present invention has several advantages compared to those of the prior art. By providing a liquid heat pack, the invention allows control of the temperature profile independently of the initial dissolution of a component in solvent. Heat packs which require that a component be kept dry prior to mixing of the components do not provide for such temperature profile control.

The heat pack of the invention retains its shape during use, because the occupied volume of the two types of zones does not change during use. This is a significant advantage when compared to certain other self-heating devices, because the shape of the heat pack does not need to be continually or periodically adjusted. This is useful, for example, for surgical and therapeutic applications in which specific parts of the body, for example, are to be heated. Other applications in which this advantage is apparent, such as rescue operations in which it is desired to warm a shock victim, are also contemplated.

The heat-producing contents of the heat pack of the invention do not fall to the bottom of the heat pack under the influence of gravity. This means that the distribution of heat within the heat pack of the invention is uniform, and the heat pack does not need to be continually kneaded to eliminate uneven heat distribution. Again, this feature is advantageous, for example, in surgical and therapeutic applications.

The time course of heating for the heat pack of the invention is relatively long. Certain known devices are based on the principle that once the chemical reactants are in contact with each other, the reaction takes place quickly. The entire heat of reaction is deposited into the other devices in a short time. These known devices act purely as heat emitters until such time as all the heat is transferred to the environment. Since the heat is deposited essentially at once, it is released over the shortest possible time, given the amount of reactants and solvent used. The heat pack of the present invention, on the other hand, produces heat over a relatively long time, due to the limits placed on diffusion of reactants within the heat pack by the gelated solution.

Upon completion of the exothermic reaction which takes place inside of the heat pack of the present invention, the pack does not contain any toxic or environmentally undesirable reactants or reaction products. Thus, the container can be safely discarded in a landfill with no danger to the environment. This is in sharp contrast to certain other self-heating devices, which contain toxic or environmentally undesirable byproducts.

The manufacture of the heat pack of the present invention is relatively simple and inexpensive. Certain known devices require complex particle coating procedures, for example, coating oxidizer crystals with sodium silicate to moderate an exothermic chemical reaction, which are obviated in the present heat pack manufacture.

Other features and advantages of the invention will be apparent from the following detailed description, and from the claims.

DETAILED DESCRIPTION OF THE INVENTION

Heat packs according to this invention comprise physically separated zones, or compartments, containing liquids that include chemical reactants. Because these packs contain liquids in all zones, and thereby differ from heat packs in which one zone contains a powder, the heat packs of this invention will be referred to as "liquid heat packs."

Figure 1:
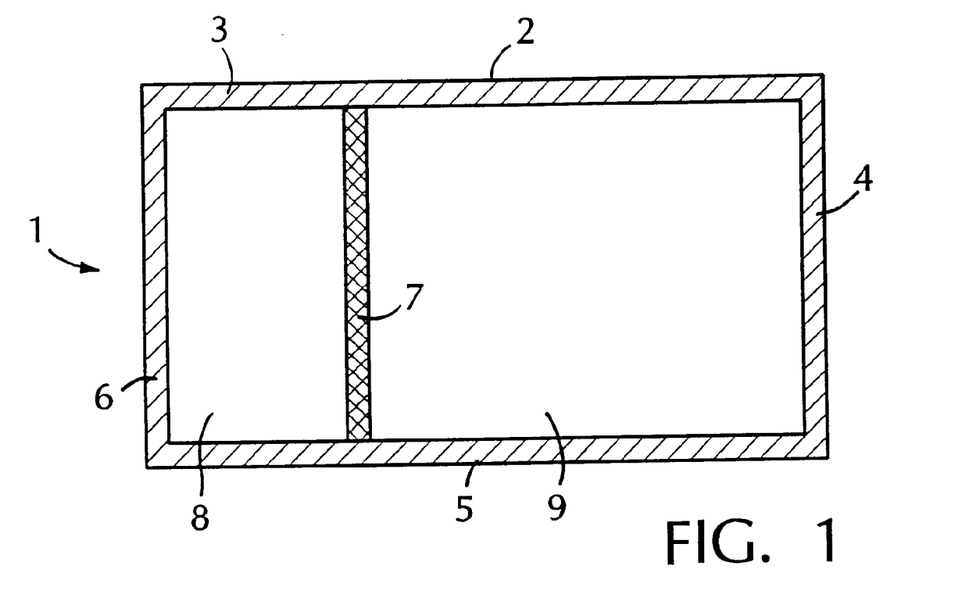
FIG. 1 shows an overhead planar view of one of the preferred embodiments of the device of the present invention with one zone of each type.

Referring to FIG. 1, there is displayed an overhead planar view of one of the preferred embodiments of the devices of the invention. The heat pack 1 is composed of a container having an upper sheet 2 and a lower sheet (not shown). The sheets are sealed together at the edges by edge seals 3, 4, 5 and 6. These edge seals are preferably made so that they are not readily opened by the consumer. A separator 7 is disposed from one edge seal of the heat pack 1 to another edge seal, thus dividing the heat pack 1 into two zones, 8 and 9. The separator is preferably made to be readily compromised by the consumer.

Figure 2:
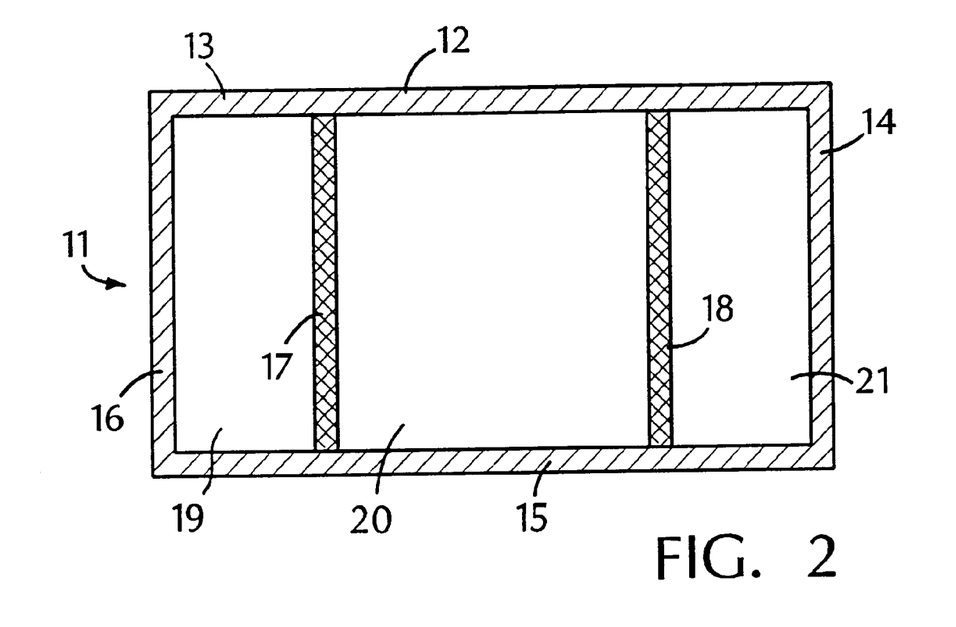
FIG. 2 shows an overhead planar view of one of the preferred embodiments of the device of the present invention with more than one zone of a given type.

Alternate embodiments of the device are also contemplated. For example, there may be more than one frangible seal, resulting in a device divided into more than two zones. This is depicted in FIG. 2, which shows a heat pack 11 composed of a container having an upper sheet 12 and a lower sheet (not shown). The sheets are sealed together at the edges by edge seals 13, 14, 15, and 16. These edge seals are preferably made so that they are no readily opened by the consumer. A pair of separators 17 and 18 are disposed from one edge seal of the pack 11 to another edge seal, thus dividing the heat pack 11 into three zones, 19, 20 and 21. The separator is preferably made to be readily compromised by the consumer.

Figure 3:
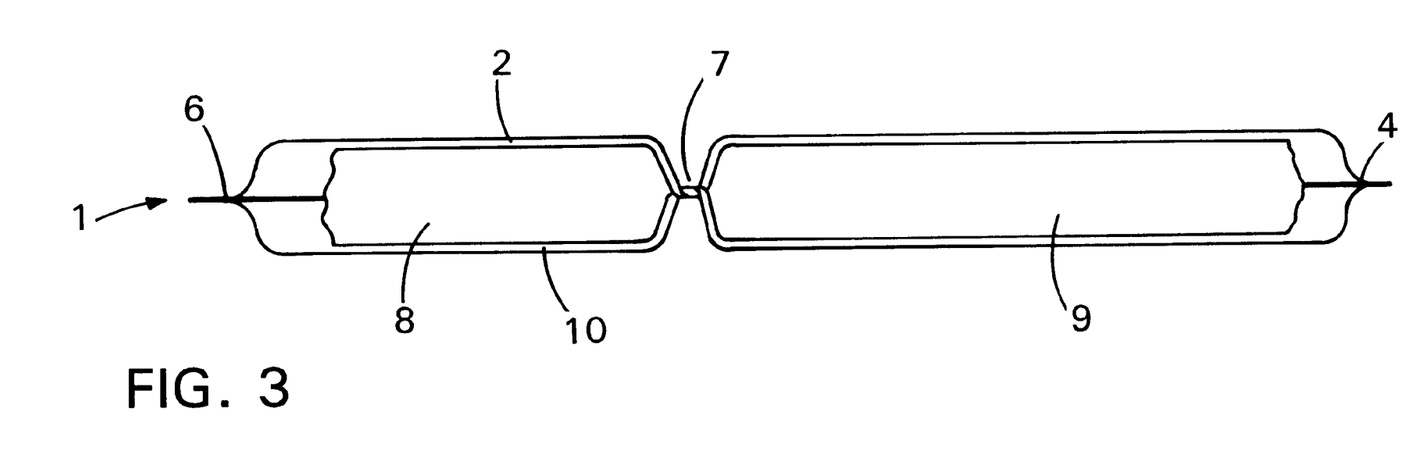
FIG. 3 shows a sectional view of one of the preferred embodiments of the invention with one zone of each type.
Figure 4:
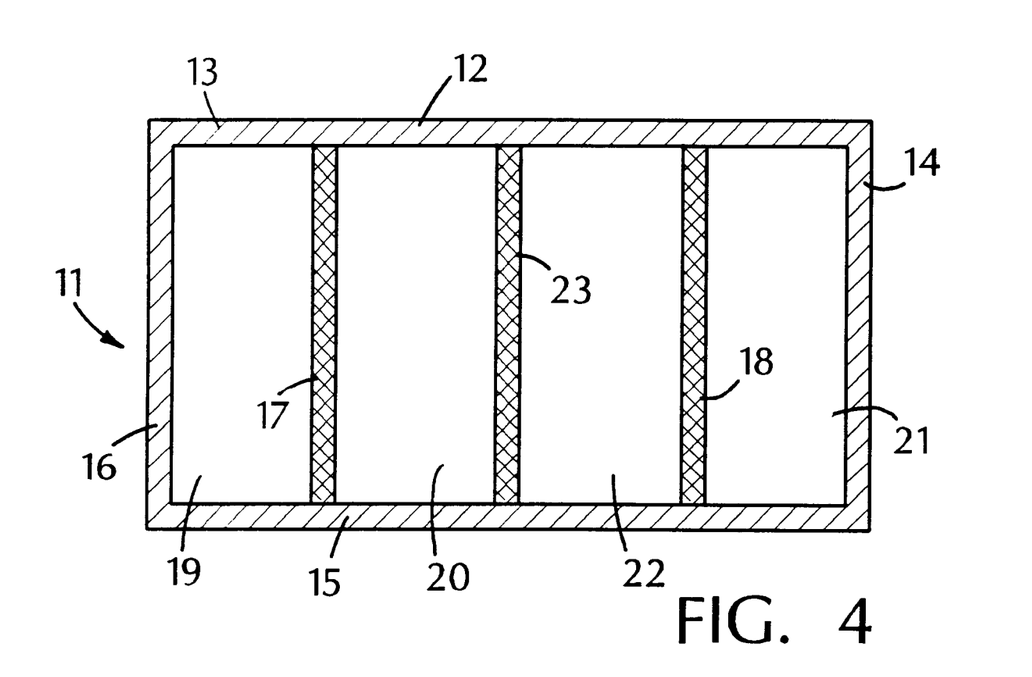
FIG. 4 shows an embodiment of the invention having a plurality of zones of each type.

FIG. 3 shows a section view of the embodiment shown in FIG. 1, with the inclusion of the lower sheet 10. Turning to FIG. 4, an embodiment of the invention having a pair of zones of one type 19 and 21, and a pair of zones of the other type 20 and 22. Separator 23 is disposed between this latter pair of zones.

In one aspect, the invention provides self-heating, disposable liquid heat packs useful for various medical and therapeutic applications, and for heating objects, for example, a container of food or drink. In another aspect, the invention provides a method for heating objects (e.g., food or drink articles, clothing, footwear) with a self-heating, disposable liquid heat pack. In another aspect, the invention provides a device useful for the warming of human or animal surgical patients. The heat packs of the invention are also suitable for therapeutic uses for human or animal subjects. In another aspect, the invention provides a device useful for hypothermic recovery of human or animal subjects.

The disposable heat pack of the present invention operates on the principle of evolution of the heat of reaction between a pair of chemical entities. In preferred embodiments, the exothermic chemical reaction is an oxidation/reduction reaction resulting upon contact of the oxidizing and reducing agent with each other. A compatible pair of chemical entities is required, one of which acts as an oxidizing agent, and the other as a fuel (reducing agent). Heat packs utilizing oxidation/reduction reactions are disclosed in U.S. Pat. No. 5,0350,230 (the "'230 patent"), which is incorporated by reference herein in its entirety. The device of the '230 patent has two separated zones. One zone contains a dry reactant, short cylinders comprising potassium permanganate crystals within a sodium silicate binder. The other zone contains an ethylene glycol/water solution. The two zones are separated, for example, by a frangible seal. When the seal between the two zones is ruptured, the fuel solution flows to the oxidizing agent pellets and reaction occurs. The rate of reaction, and hence the rate of heat production, is moderated by the binder, which selectively exposes the oxidizer to the fuel as the binder dissolves.

Many oxidizing agents are capable of generating suitable energies upon reaction with a corresponding fuel. Typical oxidizing agents include those comprising the alkali metal salts of the oxides of manganese and chromium. These include such compounds as potassium permanganate, and potassium chromate. Other suitable oxidizing agents are pyridinium dichromate, ruthenium tetroxide and chromic acid, as well as a host of other oxidizing agents known to those skilled in the art. Preferably, the oxidizing agent for use in the heat packs of the present invention comprise alkali metal salts of permanganate.

The corresponding fuels which are found suitable for the exothermic chemical reactions utilized in the devices and methods of the present invention are organic compounds. Particularly well suited organic compounds are alcohols. Alcohols are easily oxidized to carbonyl-containing compounds by the oxidizing agents described herein. The alcohols for use in the present invention are preferably primary alcohols, and preferably polyols which contain at least two hydroxyl groups. Such polyols are also readily oxidized to aldehydes and carboxylic acids. This oxidation of polyols and the simultaneous reduction of the oxidizing agent is accompanied by the release of significant amounts of heat energy. A preferred fuel for use in one of the preferred embodiments of the heat packs of the present invention is glycerine.

The fuel and oxidizing agent used in the heat packs of the present invention must be complementary. Suitable choices for these components can be any combination which is able to provide the desired characteristics of the present invention as outlined herein, meet government safety standards, and be compact. For most applications, the oxidizing agent and the fuel should conform to applicable governmental standards in case any discharge into the environment occurs, accidentally or otherwise. In one of the preferred embodiments, the oxidizing agent comprises potassium permanganate and the fuel comprises glycerine.

The use of a chemical reaction for heat generation presents significant difficulties. An oxidizing agent itself may be highly reactive and cause combustion, if not protected sufficiently. The exothermic reaction of a pack capable of generating an amount of heat needed for typical applications, if not moderated, leads to the very rapid production of heat, causing excessive temperature rise, a drawback, which can be difficult to avoid. Rapid production of heat is not the most desirable heat profile for many applications and, moreover, can be hazardous.

In light of these difficulties, it is important to moderate the production of heat in the heat pack. The rate of an unmoderated reaction is believed to be limited only by the rate of diffusion of the reactants toward each other in the mixed liquids, so that the concentrations of the reactants are directly related to the reaction rate. We moderate heat production by controlling the contact of the oxidizing agent and the fuel. This is accomplished in two ways.

One way that the rate of heat production is regulated in the device of the invention is dilution of the reactants in solvent, thereby limiting the contact of the oxidizing agent and the fuel. Dilution of either the oxidizing agent or the fuel in a solvent will reduce the overall reaction rate, and lower the maximum temperature. Dilution also increases the length of time heat is produced, due to the thermal mass of solvent.

For the devices of the invention, the solvent can be any which can solubilize both the oxidizing agent and the fuel. For such inorganic oxidizing agents, for example, alkali metal salts of permanganate, and polyhydroxy fuels, for example, as described herein, the preferred solvent is water. Water also acts as an excellent heat transfer medium in the present invention. The water used in the present invention can be tap water, although it is preferred to used controlled quality water, such as distilled or deionized water. The most preferred type of water for use in the invention is deionized water.

Another important way that we regulate the rate of heat produced by the device of the invention is by providing an environment with an increased effective viscosity, so that diffusion of the oxidizing agent and fuel toward each other takes place more slowly than it would in a solution having lower viscosity. We have found that the device of the invention can be provided with a non-fuel gelling agent that is activated to produce a non-fuel gel only when the communication between the two zones is provided. This accomplishes the aim of moderating the rate of diffusion of the reactants toward each other while not preventing their bulk mixing, thus providing a means for providing propagation of the exothermic reaction at a selectively suitable moderated rate without generating heating areas and non-heating areas. Certain other benefits are provided as well. In particular, the initial reaction rate is high prior to gel formation. This permits rapid temperature rise initially, before the gel moderates the reaction rate. The gelling agent can be placed in either the first type of zone which includes the oxidizing agent, or the second type of zone, which includes the fuel. In one of the preferred embodiments, the gelling agent is included in the zone of the container which holds the fuel. After operation or compromise of the separator between the two types of zones, and the subsequent establishment of communication between them, the oxidizing agent is able to come in contact with the fuel and the gelling agent.

Preferred gelling agents are those which are able to form a gel only upon activation of the device. Premature gelation of the contents of the heat pack container would limit the ability of the container to conform to the shape of objects to be heated. Premature gelation would also unduly limit the extent of reaction by making some fuel practically unavailable for reaction with the oxidizing agent. In preferred embodiments of the invention, the exothermic chemical reaction and the gelation begin substantially simultaneously.

Gelling agents for use in the present invention are non-fuels. They can be inorganic gelling agents. Organic gelling agents tend to serve as fuels for the oxidizing agents and are thereby destroyed, eliminating the gelation desired in the present invention. Thus, a general requirement for the gelling agents to be used in the heat packs of the invention is that they not be fuels for the chemical reaction. Suitable inorganic gelling agents are metal oxides or alkali metal salts of metal oxides. These include zinc oxide, tin oxide, titanium oxide, zirconium oxide, and silicates and aluminates. We have found that inorganic gelling agents comprising silicates give suitable results. Preferred inorganic gelling agents are those which are soluble in a solvent, generally an inorganic solvent, such as water. Desirably, the silicates would be soluble in the solvent which may be chosen for either zone of the container. When the solvent is water, one preferred embodiment uses sodium silicate, such as sodium silicate solution ($Na_2SiO_3$), such as that available from J. T. Baker (Stock No. 3877-01), or Aldrich Chemical Co., Inc. (Stock No. 33,844-3).

In the present invention, providing communication between the zone containing oxidizing agent and the zone containing fuel initiates the gelation of the contents of the heat pack. The exothermic chemical reaction itself can initiate the gelation of the gelling agent. While not wishing to be bound by any particular theory, we believe that upon oxidation of the polyhydroxy fuel by an inorganic oxidizing agent, the pH of the aqueous environment drops to acidic values. We believe that this pH drop triggers the conversion of the inorganic gelling agent, e.g., sodium silicate, to a gel, which thereby creates the desired gelation in the heat pack of the invention. Detailed information on gelation technology is available, e.g., in scientific publications such as Livage, J. et al., Prog. Solid St. Chem., 18:259 (1988), which is hereby incorporated in its entirety.

As described above, communication between the zone containing oxidizing agent and the zone containing fuel will initiate an exothermic chemical reaction. The exothermic chemical reaction causes the temperature of the interior of the heat pack to rise. Heat is transmitted by convection through the liquid medium in the heat pack to the exterior surfaces of the device, where it is further transmitted to other bodies, according to the specific application for which the heat pack can be employed. A characteristic feature of the heat pack is the attainment of an operating temperature which is measured on the surface of the heat pack. The operating temperature depends directly on the concentrations of the oxidizing agent and the fuel, and can be moderated by gel formation, as described herein. Thus, the operating temperature of the heat pack can be regulated to a desired level varying the concentrations of oxidizing agents, fuels and gelling agents. Only routine experimentation is required to select appropriate concentrations for a particular use. Suitable operating temperatures can vary from about 20° F. above ambient temperature to about 120° F. above ambient temperature.

Gelation is required to have certain functional characteristics in order to produce the moderating effects desired in the heat packs of the invention. Gelation must occur within a time sufficient to prevent the exothermic chemical reaction from raising the operating temperature of the heat pack above a predetermined maximum temperature ($T_{max}$) The $T_{max}$ will lie above the operating temperature of the heat pack. For use in contemplated applications, $T_{max}$ for the heat packs of this invention will lie from about 1° F. to about 50° F. above the desired operating temperature of the pack. The predetermined maximum temperature will depend on the particular application for which the heat pack is employed. Considerations may be given to comfort or safety to the user, integrity of the container, or other factors apparent to persons skilled in the art relating to the heating of food or drinks. The minimum concentration of the gelling agent is to be chosen so that sufficient gelation takes place in the heat pack, since moderation of the exothermic chemical reaction is achieved through formation of a gel.

A more concentrated gelling agent can generally produce a gel more rapidly. The length of time required to form a gel after communication between the two zones in the heat pack of the invention is established is referred to as the gelation time. The more rapidly a gel forms, the greater its efficacy in preventing the temperature of the interior of the heat pack from overshooting the allowed $T_{max}$.

One skilled in the art will readily be able to determine concentrations of gelling agent which will result in sufficient gelation at a time soon enough to prevent the temperature of the device from exceeding the $T_{max}$ suitable for a given application.

In a preferred embodiment, an excess of fuel will be present in the reaction mixture to assure continuous exposure of the fuel to the oxidizing agent. This also ensures that upon completion of the reaction of the oxidizing agent, there are no soluble toxic residues remaining in the container. Disposal of the container in a landfill is made possible by this feature.

To initiate the exothermic oxidation reaction, the fuel and oxidizing agent must come in contact with each other. This is preferably accomplished in the present invention by opening, selectively perforating, rupturing or otherwise compromising the separator between the zones containing the oxidizing agent and fuel/gelling agent, so that the oxidation reaction partners contact each other. In a preferred embodiment, oxidizing agent is transferred into the zone containing fuel so as to come into contact with the fuel. However, it is also contemplated that the fuel is transferred into the zone containing the oxidizing agent. Either zone may contain the gelling agent. It is preferred that the separator comprises a material that allows its rupture, perforation, or compromise when the container is manually deformed. In embodiments which comprise more than a single pair of container zones, it is contemplated that the heat pack of the invention comprise an appropriately increased number of separators, so that communication may be established between zones of each type, sufficient to provide the heat desired. A plurality of separators can also be employed in embodiments utilizing only a single pair of zones. The invention is not limited by the juxtaposition or configuration of the zones in the heat pack.

Pressure against or along the separator selectively ruptures, perforates, or otherwise compromises the separator, while leaving the outer surfaces of the container, and the surfaces surrounding the container and oxidizer and fuel/gelling agent zones intact. The separator can be comprised of any of a number of functional configurations. In a preferred embodiment, the separator comprises a brittle or weakened wall extending between the zone containing oxidizing agent and the zone containing fuel, which is manually separable, thereby compromising the separator. In another preferred embodiment, the separator can be compromised by the use of pull tabs. When pulled, the pull tabs compromise the separator and communication is provided between the oxidizing agent zone and the fuel/gelling agent zone. In a less preferred embodiment, the separator comprises a hole with a stopper, which is removable when pressure is applied to it. Communication is again provided through the separator. We most prefer that the separator comprises a wall having weakened or thin areas which rupture when pressure is applied against it. In another embodiment, the separator can comprise a wall having a plurality of perforations which rupture under applied pressure and expose the fuel/gelling agent to the oxidizing agent. The separator can likewise consist of a movable disk or cap, pierced or otherwise, or a valve, such as a frangible valve.

Alternatively, the separator can be configured to form one or preferably a plurality of fissures or slits when the separator is subjected to external pressure. The fissures can extend inwardly from the edges or perimeter of the separator, or they can be located intermediate the edges or perimeter of the separator. However, any adequate means for compromising the separator can be used in the present invention. Persons skilled in the art will recognize other possible variants.

The container preferably comprises a flexible material which is not deleteriously affected by either the oxidizing agent or the fuel/gelling agent or any solvent which is chosen for the individual zones, and which is resistant to the temperature to be achieved. Such materials include polyethylene, polypropylene, polyester (such as MYLAR®, film obtainable from DuPont) aluminum, aluminized polymer film, and other conventional plastic or other packaging materials suitable for containing heated liquids such as rubber, vinyl, vinyl-coated fabric and polyethylene. A thickness of about 0.02 mm to about 0.1 mm has been found to be satisfactory using clear vinyl.

The container can be constructed of thin, flexible, thermally conductive material comprising an upper layer and a lower layer which are bonded together at the edges to form an hermetically sealed, substantially planar envelope. In a preferred embodiment, the thermally conductive material is a metal foil, such as one composed substantially of aluminum or copper, or a metallized plastic film such as aluminized polyester, for example MYLAR®. The edges of the material can be bonded together by any suitable means, for example, soldering, heat sealing, ultrasonic welding, solvent welding, fold sealing, or the use of adhesives.

During fabrication of the heat pack, the container preferably comprises an open end or side at each of the zones for the introduction of the fuel/gelling agent and oxidizing agent, respectively. The other sides or edges can be sealed before this introduction. After addition of the fuel/gelling agent and oxidizing agent to the container, the open sides are sealed to make the container fluid- and air-tight. The size and shape of the container, as well as the juxtaposition and configuration of zones within the container, will vary according to the application for which it is used. Therefore, alternative assembly procedures can be required to properly assemble the heat pack. For example, one type zone can be necessarily sealed before the loading of the other type of zone, in e.g., an annular arrangement of zones. A stacked arrangement of zones can also be employed. The invention is not limited by the arrangement of zones within the container.

After assembly and prior to its use, the heat pack is in a static condition, with the heat pack preferably disposable after a single use. In an alternative embodiment of the present invention, a plurality of oxidizing agent zones and/or fuel/gelling agent zones are contemplated for use in the heat pack of the present invention. As previously mentioned, more than one separator could be used in these embodiments, as well as embodiments having only a single pair of zones.

The heat pack of the present invention can be adapted to be used in surgical applications, such as in human or veterinary surgery. During surgery, core body temperatures often drop to undesirable levels. The heat pack of the present invention can easily be used to warm patients. For these and other applications, the heat pack preferably includes a fastening means which allows the initial positioning of the heat pack, e.g., onto a limb. Subsequent activation of the device can take place without further positional adjustment. Suitable fastening means include straps, adhesive tape, or reusable strips such as VELCRO® strips. Such surgical applications can desirably be fulfilled if the heat pack is designed as a sleeve which is dimensioned to be placed around a limb, such as the leg of a human, horse, dog, or any other animal for which veterinary surgery is carried out. Or flat heat packs can be inserted into a fabric sleeve or wrap. Desirably, the sleeve diameter is adjustable, permitting the use of the same sleeve on a variety of patients. Alternately, the heat pack is designed as a pad, allowing extensive bodily surfaces such as the back or chest of a human or animal to be heated.

The heat pack of the present invention can be adapted to be used in, and adapted to be used in, therapeutic applications. Many types of injury are most desirably treated through the application of heat. These include muscle and ligament strains and sprains, as well as such afflictions as rheumatism, arthritis, and the like. Such applications of the heat pack would also require the heat pack to be fashioned as a sleeve or a pad, and include fastening means, such as those described above.

The heat pack of the present invention can also find use in remote wilderness areas for recreational purposes, or in rescue operations in any area, where compact, self-heating devices are desired. The heat pack can be used to warm shock victims, or to treat or prevent frostbite. The heat pack can also be designed to heat food, or footwear, for example. In such applications, the heat pack can be designed to assume the appropriate shapes for these uses.

The invention also features a method of heating an object with a self-heating, disposable liquid heat pack. The method consists of providing a heat pack such as described above, activating the heat pack by compromising the separator, and subsequently putting the exothermic reaction and gelation thereby initiated to practical use in heating an object. In some embodiments, the heat pack can be integral with a container for a substance to be heated, such as a container for food or drink. In other embodiments, the heat pack can be simply added on to the object to be heated, or adapted to be fit to the object to be heated.

The invention will be further described in the following examples, which do not limit the scope of the invention described in the claims.

EXAMPLES

The following examples are illustrative of some specific embodiments of the invention, and performance characteristics of the invention.

Example 1

Heat Pack for Use with a Surgery Recovery Reheater

A heat pack for use with a surgery recovery reheater contained the following ingredients: 25 grams of finely divided USP Grade potassium permangante, 15 ml of sodium silicate solution (41 degrees Baume'), 60 ml glycerine, and 806 ml deionized water. A vinyl container measuring about 12 inches by 13 inches was prepared, and when filled and sealed, the container's thickness was substantially thinner than either of its other dimensions. The container had a zone for the oxidizing agent (potassium permanganate), two fuel (glycerine) zones, and a frangible seal between the oxidizing agent zone and each of the fuel zones. The gelling agent (sodium silicate solution) was included in the oxidizing agent zone. A suitable distribution of water between the zones was determined through a few trials, and the following split worked well. The single oxidizing agent/gelling agent zone contained 746 ml water and the entire amount of oxidizing agent and gelling agent, and each of the two fuel zones contained 30 ml water, and 30 ml of glycerine. The container was sealed and was thereafter ready for use.

Upon activation of the heat pack by compromising the frangible seal, the heat pack reached an operating temperature of 38° F. above ambient temperature. This operating temperature was maintained for approximately 30 minutes, after which the device cooled back to ambient temperature over the course of 60 minutes.

We have successfully tested other embodiments of the heat pack of the invention for other applications. For human therapy, a smaller heat pack (approximately 6.5 inches by 8 inches) was designed and produced. For this heat pack, the ingredients were 11 grams potassium permanganate, 11 ml sodium silicate solution (41 degrees Baume'), 32 ml glycerine, and 175 ml deionized water. In this embodiment, the container had a single oxidizing agent zone and a single fuel zone. In this embodiment, the gelling agent was included in the fuel zone. In this particular pack, which included Surlyn®, a film material available from DuPont and believed to be an ionomer, as the frangible seal material, the alternative of including the gelling agent with the oxidizing agent was found to degrade this particular seal material. Of course, other sealing materials and arrangements are possible. Upon operation, this heat pack exhibited an operating temperature of 70° F. above ambient temperature.

Another embodiment of the heat pack was designed and produced for use in veterinary applications. This container was also approximately 6.5 inches by 8 inches, with a single zone for each of the oxidizing agent and fuel. The ingredients of this heat pack were 16 grams potassium permanganate, 12 ml sodium silicate solution, 36 ml glycerine, and 177 ml deionized water.

This heat pack exhibited an operating temperature of 90° F. above ambient temperature. Upon comparison of the performance of this heat pack with an equal weight of water, we observed that over a 30 minute period, the heat pack cooled from 88° F. above ambient temperature to 63° F. above ambient temperature, a 25° F. drop in temperature. The water dropped from 88° F. above ambient temperature to 47° F. above ambient temperature, a 41° F. drop in temperature. Thus, the heat pack of the invention provides long-lasting heating properties which are superior to those of an equal weight of water.

Example 2

Acute Toxicity of Activated Heat Pack Solution to Fathead Minnow (*Pimephales promelas*)

A study of the acute toxicity of the contents of a previously activated heat pack was conducted according to standard procedures of the American Society for Testing and Materials ("ASTM") according to the regulations of the Environmental Protection Agency ("EPA"). These tests are detailed in ASTM Designation E729-88a (Standard Guide for Conduction Acute Toxicity Tests with Fishes, Macroinvertebrates, and Amphibians, 1988). Generally, the test is conducted in 19 liter glass jars containing 15 liters of test solution and 10 fathead minnows. Three dilutions of previously activated heat pack contents and a control solution were introduced to the glass jars. The dilutions corresponded to 1,100, and 1000 mg of previously activated heat pack contents per liter of test solution. After 96 hours of testing, there were no mortalities in any of the glass jars. This test demonstrated the non-toxicity of the used heat packs and their suitability for disposal in landfill facilities.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A disposable heating device comprising:
    a disposable container having at least one liquid impermeable first zone and at least one liquid impermeable second zone;
    a first liquid comprising an oxidizing agent in the at least one first zone;
    a second liquid comprising a fuel in the at least one second zone;
    a non-fuel gelling agent solution in at least one of the zones;
    a separator disposed between the at least one first zone and the at least one second zone, the separator being operable to provide communication between the zones,
    wherein communication between the zones causes mixing of the liquids therein and initiates an exothermic reduction-oxidation reaction to produce heat in said container,
    wherein communication between the zones initiates gelation of said gelling agent within said container to produce in said container a non-fuel gel that moderates the rate of said reaction independently of dissolution of said gelling agent,
    and wherein the amount of said gelling agent is sufficient to produce said gel sufficiently rapidly to prevent said exothermic reaction from causing the temperature of the container to overshoot a predetermined maximum temperature.

2. The heating device of claim 1, wherein the gelation is initiated by the exothermic chemical reaction.

3. The heating device of claim 1, wherein at least one of the first and second liquids is an aqueous liquid, resulting in said chemical reaction occurring in an aqueous environment.

4. The heating device of claim 1, wherein the container comprises material resistant to the exothermic chemical reaction.

5. The heating device of claim 4, wherein the container comprises a thin-walled envelope that conforms to the shape of its surroundings.

6. The heating device of claim 1, wherein the fuel comprises a polyhydroxy compound.

7. The heating device of claim 6, wherein the polyhydroxy compound comprises glycerine.

8. The heating device of claim 1, wherein the non-fuel gelling agent is an inorganic compound.

9. The heating device of claim 8, wherein the inorganic compound is an alkali metal salt of a silicate.

10. The heating device of claim 9, wherein the oxidizing agent comprises an alkali metal salt of permanganate.

11. The heating device of claim 10, wherein the fuel comprises a polyhydroxy compound.

12. The heating device of claim 1 further comprising a plurality of first zones and a plurality of second zones.

13. The heating device of claim 1, wherein the separator is a single-use, frangible membrane.

14. The heating device of claim 1, wherein the oxidizing agent consists of an uncoated oxidizing agent.

15. The heating device of claim 1, wherein the gelling agent is present in the second zone.

16. A disposable heating device comprising:
    a disposable container having at least one liquid impermeable first zone and at least one liquid impermeable second zone;
    a liquid comprising potassium permanganate in the at least one first zone;
    a liquid comprising glycerine in the at least one second zone;
    a solution of sodium silicate in at least one of the zones;
    a single-use frangible membrane disposed between the at least one first zone and the at least one second zone, the single-use frangible membrane being operable to provide communication between the zones,
    wherein communication between the zones causes mixing of the liquids therein and initiates an exothermic chemical reaction to produce heat in said container,
    wherein communication between the zones initiates gelation of said gelling agent within said container to produce in said container a non-fuel gel that moderates the rate of said chemical reaction independently of dissolution of said gelling agent,
    and wherein the amount of said gelling agent is sufficient to produce said gel sufficiently rapidly to prevent said exothermic reaction from causing the temperature of the container to overshoot a predetermined maximum temperature.

17. A method of heating objects, comprising the steps of:
a) providing a heating device in contact with an object to be heated, said heating device comprising:
   1) a container having at least one liquid impermeable first zone and at least one liquid impermeable second zone;
   2) a liquid comprising oxidizing agent in the at least one first zone;
   3) a liquid comprising a fuel in the at least one second zone;
   4) a non-fuel gelling agent solution in at least one of the zones;
   5) a single-use frangible membrane disposed between the at least one first zone and the at least one second zone, the being operable to provide communication between the zones, wherein communication between the zones causes mixing of the liquids therein and initiates a reduction-oxidation reaction to produce heat in said container, wherein communication between the zones initiates gelation of said gelling agent within said container to produce in said container a non-fuel gel that moderates the rate of said reaction independently of dissolution of said gelling agent, and wherein the amount of said gelling agent is sufficient to produce said gel sufficiently rapidly to prevent said reaction from causing the temperature of the container to overshoot a predetermined maximum temperature; and
b) compromising the single-use frangible membrane to permit contact between the zones, thereby initiating said reduction-oxidation reaction and said gelation.

18. The method of claim 17, wherein the object to be heated is a food or drink.

19. The method of claim 17, wherein the object to be heated is a part of the body of a human or animal surgical patient.

20. The method of claim 17, wherein the object to be heated is an article of clothing or footwear.

21. The heating device of claim 3, wherein the gelatin is initiated by a pH change in the aqueous environment.

22. The heating device of claim 5, wherein the container comprises a polymeric material.

23. The heating device of claim 1, wherein the oxidizing agent comprises an alkali metal salt of permanganate.

24. The heating device of claim 23, wherein the alkali metal salt of permanganate is mixed with a solvent.

25. The heating device of claim 24, wherein the solvent is water.

26. The heating device of claim 7, wherein the glycerine is mixed with a solvent.

27. The heating device of claim 26, wherein the solvent is water.

28. The heating device of claim 1, wherein the exothermic chemical reaction is a reduction-oxidation reaction.

29. The heating device of claim 16, wherein the separator comprises a single-use frangible membrane.

* * * * *

UNITED STATES PATENT AND TRADEMARK OFFICE
CERTIFICATE OF CORRECTION

PATENT NO.       : 6,116,231
APPLICATION NO.  : 09/021927
DATED            : September 12, 2000
INVENTOR(S)      : Martin W. Sabin, Cullen M. Sabin and Barney J. Guarino Page 1 of 1

It is certified that error appears in the above-identified patent and that said Letters Patent is hereby corrected as shown below:

In the claims:

Col. 13, line 15, insert --single-use frangible membrane-- after "zone, the".

Signed and Sealed this

Twentieth Day of March, 2007

JON W. DUDAS
*Director of the United States Patent and Trademark Office*